(12) United States Patent
Pichavant et al.

(10) Patent No.: US 9,831,937 B2
(45) Date of Patent: Nov. 28, 2017

(54) COMMUNICATION SYSTEM AND METHOD FOR THE TRANSMISSION OF AUDIO DATA SIGNALS FROM AN AIRCRAFT COCKPIT TO A GROUND STATION

(71) Applicant: Airbus Operations SAS, Toulouse (FR)

(72) Inventors: Claude Pichavant, Toulouse (FR); Francois De-La-Tousche, Toulouse (FR)

(73) Assignee: Airbus Operations (SAS), Toulouse (FR)

( * ) Notice: Subject to any disclaimer, the term of this patent is extended or adjusted under 35 U.S.C. 154(b) by 0 days.

(21) Appl. No.: 15/444,562

(22) Filed: Feb. 28, 2017

(65) Prior Publication Data

US 2017/0257160 A1    Sep. 7, 2017

(30) Foreign Application Priority Data

Mar. 3, 2016  (FR) ...................................... 16 51801

(51) Int. Cl.
  *H04L 12/58*  (2006.01)
  *H04B 7/185*  (2006.01)
  *H04R 1/10*   (2006.01)
  *H04R 29/00*  (2006.01)

(52) U.S. Cl.
  CPC ......... *H04B 7/18508* (2013.01); *H04R 1/105* (2013.01); *H04R 1/1008* (2013.01); *H04R 1/1041* (2013.01); *H04R 29/00* (2013.01)

(58) Field of Classification Search
  CPC ........ G08G 1/16; G08G 5/0013; G08B 19/00; H04H 20/02; H04H 20/62; H04L 12/1895

USPC ............... 340/945; 381/74; 455/575.2, 412.1
See application file for complete search history.

(56) References Cited

U.S. PATENT DOCUMENTS

| | | |
|---|---|---|
| 2004/0027255 A1 | 2/2004 | Greenbaum |
| 2007/0297618 A1 | 12/2007 | Nurmi et al. |
| 2013/0169451 A1 | 7/2013 | Steinmetz |
| 2014/0072136 A1* | 3/2014 | Tenenbaum ........... G08B 21/06 381/74 |

OTHER PUBLICATIONS

French Search Report, dated Oct. 20, 2016, priority document.

* cited by examiner

*Primary Examiner* — Tu X Nguyen
(74) *Attorney, Agent, or Firm* — Greer, Burns & Crain, Ltd.

(57) ABSTRACT

A communication system installed in an aircraft, the system comprising a transmitter configured to transmit audio data signals to a ground recording station provided with memories for the recording of the data, at least one audio assembly per pilot of the aircraft for transmitting and receiving audio data signals, a CVR recorder and an audio management unit connected to each audio assembly, to the CVR recorder and to the transmitter, the unit being configured to transfer the audio signals received or transmitted by an audio assembly to the transmitter and to the CVR recorder. Each audio assembly comprises an in-use detection system connected to the transmitter and configured to transmit to the transmitter a signal representative of the in-use state of the audio assembly. The transmitter transmits the audio data signals received from the management unit to the ground recording station on reception of the signal.

5 Claims, 5 Drawing Sheets

COMMUNICATION SYSTEM AND METHOD FOR THE TRANSMISSION OF AUDIO DATA SIGNALS FROM AN AIRCRAFT COCKPIT TO A GROUND STATION

CROSS-REFERENCES TO RELATED APPLICATIONS

This application claims the benefit of the French patent application No. 1651801 filed on Mar. 3, 2016, the entire disclosures of which are incorporated herein by way of reference.

BACKGROUND OF THE INVENTION

The present invention relates to a communication system and a method for the real time transmission of audio data signals from an aircraft cockpit to a ground station for recording the data.

Each aircraft comprises a CVR (Cockpit Voice Recorder: cockpit conversations recorder) recorder which records the sounds in the cockpit namely the conversations between the pilots inside the cockpit (pilot/co-pilot/third occupant), the background noise of the cockpit (alarm sounds for example), as well as the conversations the pilots have with an entity outside of the aircraft (ATC air traffic control, ground mechanics, etc.).

With the objective of improved management of the monitoring of communications in aircraft, it is envisaged to send, via satellite communication, the data relative to the sounds in the cockpit to a ground station which would record them, in addition to the storage of these data in the CVR recorder onboard the aircraft.

The data rate required for the transmission of the audio data is high whereas the bandwidth of the satellite link between the aircraft and the ground station is limited. Because of this, the transmission to the ground station of the data recorded by the CVR recorder gives rise to a technical problem. One of the objectives of the invention is to totally or partially eliminate this disadvantage.

SUMMARY OF THE INVENTION

For this purpose, the invention relates to a communication system installed in an aircraft, the system comprising a transmitter allowing the transmission of audio data signals to a ground recording station provided with memories for the recording of the data, at least one audio assembly per pilot of the aircraft for transmitting and receiving audio data signals, a CVR recorder and an audio management unit connected to each audio assembly, to the CVR recorder and to the transmitter, the unit being configured for simultaneously transferring the audio signals received or transmitted by an audio assembly to the transmitter and to the CVR recorder, each audio assembly comprising an in-use detection system connected to the transmitter and configured for transmitting to the transmitter a signal representative of the in-use state of the audio assembly, the transmitter transmitting the audio data signals received from the management unit to the ground recording station on reception of the signal.

Thus, according to the invention, only the audio data signals transmitted or received by an audio assembly used by a pilot are transmitted to the ground station for recording. Consequently, the audio data signals transmitted or received by the unused audio assemblies (which are always recorded in the CVR recorder) are not transmitted to the ground station. The use of the bandwidth of the satellite link is therefore optimized.

BRIEF DESCRIPTION OF THE DRAWINGS

Other advantages and features of the invention will become apparent in the detailed and non-limiting description below. This description is given with reference to the appended drawings in which.

DETAILED DESCRIPTION OF THE PREFERRED EMBODIMENTS

Figure 1:
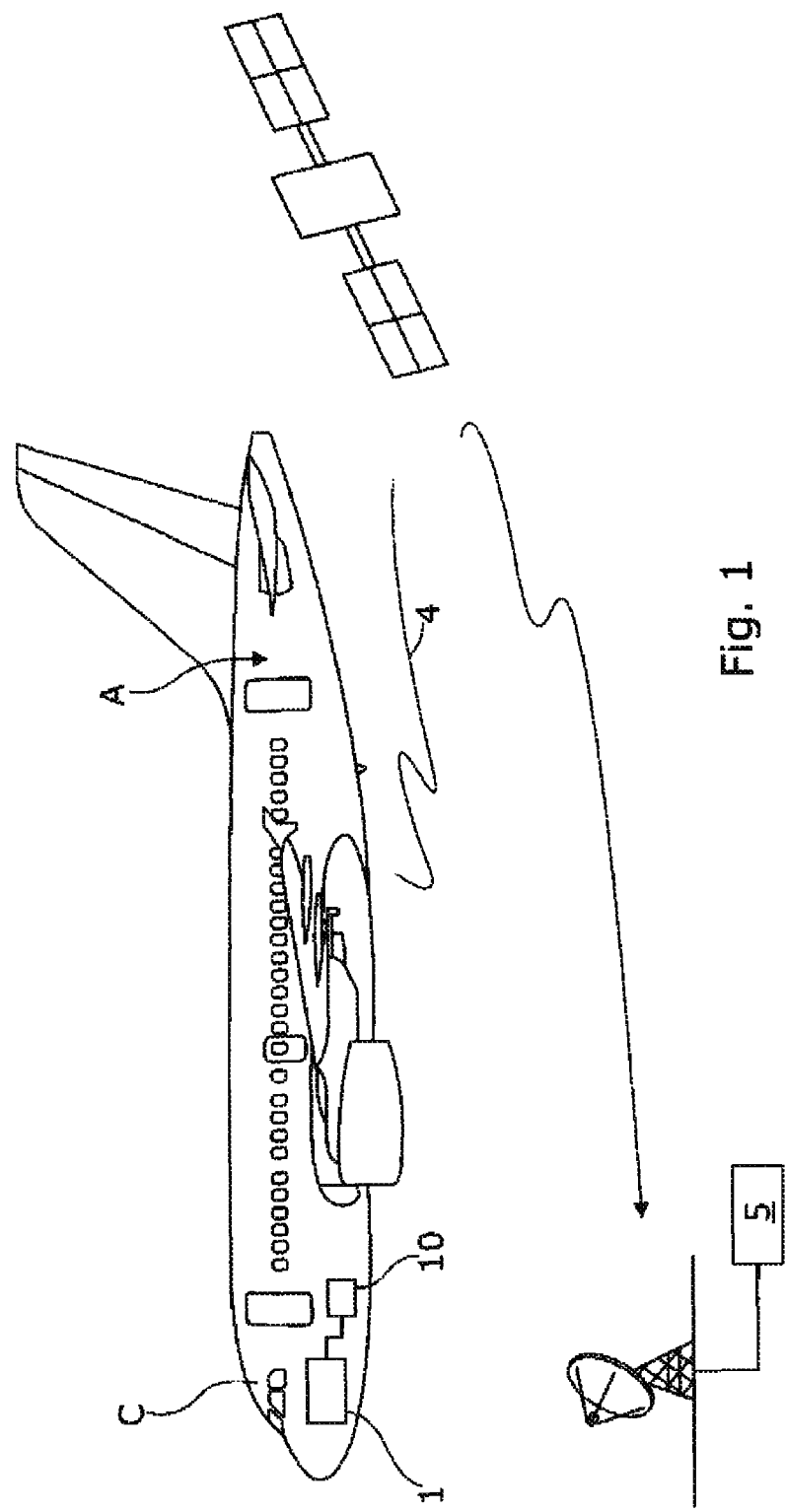
FIG. 1 is a diagrammatic view of an aircraft equipped with a communication system according to the invention for transmitting audio data signals to a ground station configured for recording the signals.
Figure 2:
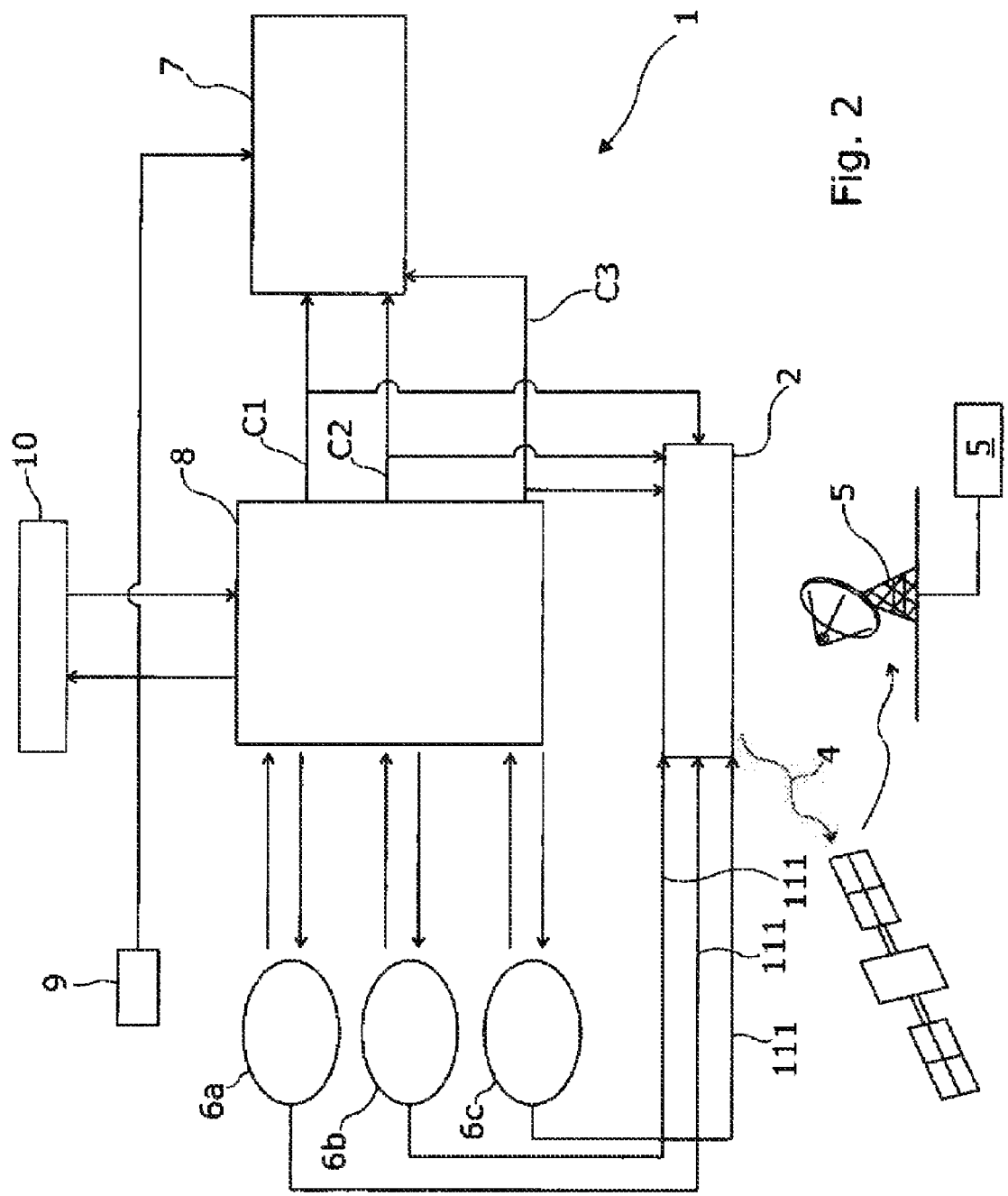
FIG. 2 is a diagrammatic view of the communication system of the invention shown in FIG. 1, the communication system comprising several audio assemblies where each assembly can be used by a pilot for transmitting and receiving audio data signals.

With reference to FIGS. 1 and 2, a communication system 1 according to the invention installed in an aircraft A comprises a transmitter 2 making it possible to transmit, by means of a satellite link 4, audio data signals to a ground recording station 5 provided with memories (not shown) for recording the data, at least one audio assembly 6a-c per pilot for transmitting and receiving audio data signals, a microphone 9 for recording the background noise in the cockpit C of the aircraft, a CVR recorder 7, and an audio management unit 8 having the task of distributing the audio signals between the various components of the communication system.

The audio management unit 8 is connected to each audio assembly 6a-6c, to the transmitter 2, to the CVR recorder 7 and to radio means 10 (transmitter) of the aircraft by which audio signals are sent to or received from entities outside of the aircraft (not shown) such as, for example, air traffic control (ATC).

It should be noted that the communication system 1 shown in FIG. 2 comprises three audio assemblies 6a-6c, with a first audio assembly 6a dedicated to the pilot, a second audio assembly 6b dedicated to the copilot and a third audio assembly 6c dedicated to the third occupant. Each audio assembly 6a-6c is independent of the other audio assemblies so that each pilot can communicate with an entity (audio assembly or radio means) different from the one with which another pilot is communicating.

The distribution of the audio signals in the communication system 1 is as follows:

an audio data signal transmitted by the microphone 9 is sent directly to the CVR recorder 7 for its recording;

an audio data signal transmitted by an audio assembly 6a-6c to another audio assembly 6a-6c or to the radio means 10, or a signal coming from another audio signal 6a-c or from the radio means 10 and to an audio assembly 6a-c is sent to the management unit 8 which transmits it simultaneously, via a dedicated channel, to that audio assembly, to the CVR recorder 7 for its recording and to the transmitter 2. As shown in FIG. 2, the management unit 8 sends audio data signals from the first/second/third audio assembly to the CVR recorder 7 and to the transmitter 2 via, respectively, a first channel C1/a second channel C2/a third channel C3.

Figure 3:
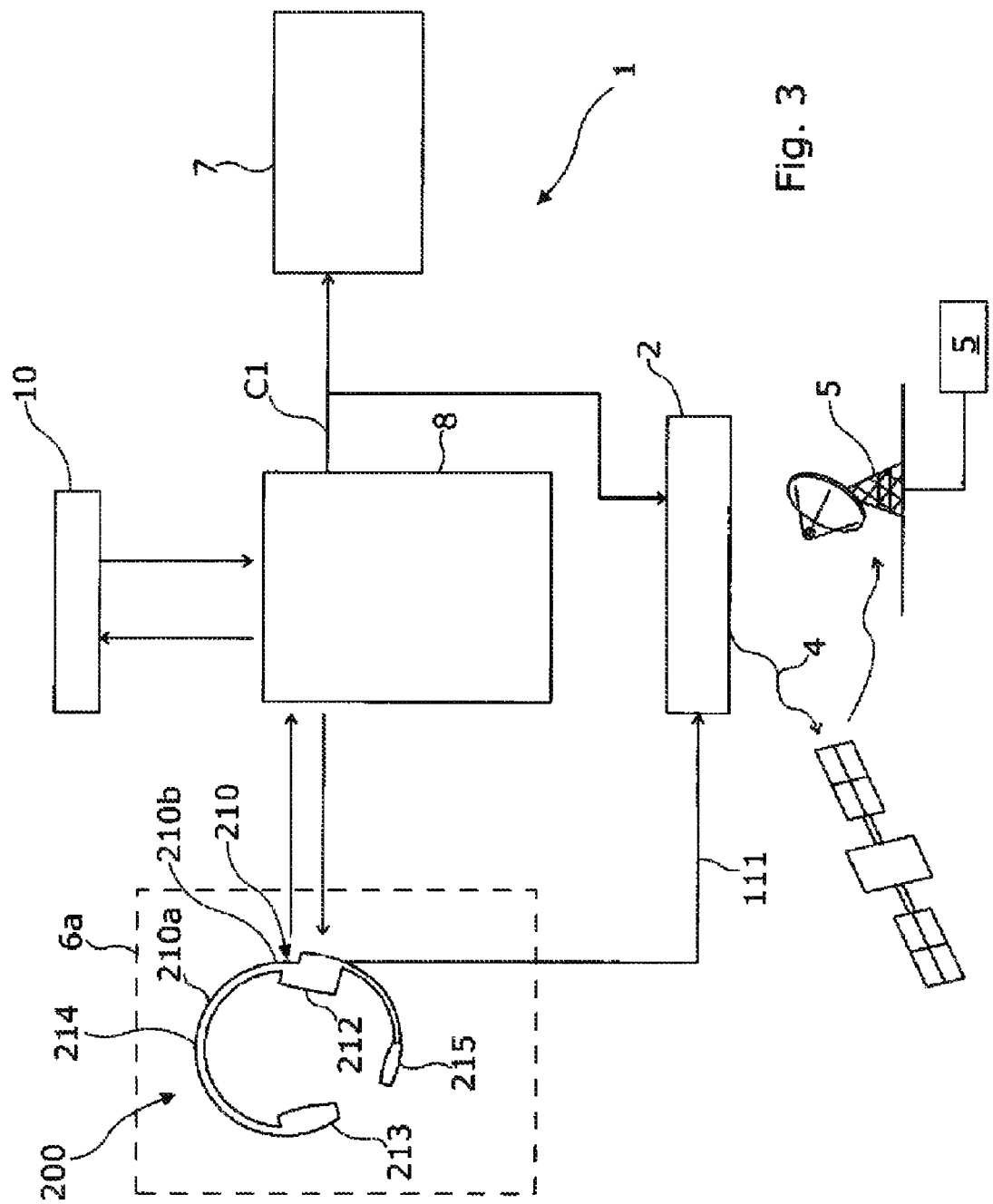
FIG. 3 is a view similar to FIG. 2 according to an embodiment of the invention in which an audio assembly is an audio headset provided with a microphone.

The invention comprises optimizing the use of the bandwidth of the satellite link 4 by activating the communication between the communication system 1 and the ground station 5 on the condition that a pilot is using the audio assembly 6a-c which is dedicated to him For this purpose, each audio assembly 6a-c, such as for example the assembly 6a shown in FIG. 3, comprises an in-use detection system 210 connected directly to the transmitter 2 via a data link 111. The in-use detection system 210 transmits, to the transmitter 2, a signal indicative of the in-use or not-in-use state of the audio assembly and the transmitter 2 activates the communication between the communication system 1 and the ground station 5 on condition that the signal that it receives from the in-use detection system 110 indicates that the audio assembly 200 is being used by the pilot. For example, the signal transmitted by the system 210 for detecting the use of an assembly to the transmitter 2 is a digital signal comprising a PORT bit set to 1 (signal representing the in-use state of the audio assembly) if the audio assembly is being used and to 0 if not (signal representing the not-in-use state of the audio assembly).

As can be seen in FIG. 3, the audio assembly 6a is, for example, a headset provided with two loudspeakers, left 212 and right 213, connected by a headband 214 able to clamp the head of a pilot who is wearing the headset, and a microphone 215 fixed to one of the loudspeakers. This headset 200 will be referred to as a "boomset" in the rest of the description.

When the boomset 200 is not worn, the headband 214 naturally has a curvature which gives a separation narrower than the width of the average head of a person. On the contrary, when the boomset 200 is worn, the headband 214 deforms because of the width of the pilot's head and the curvature of the headband increases. The in-use detection system 210 comprises a detector 210a of the strain gauge type arranged on the headband 214, as well as control means 210b, for example a microcontroller arranged on an earphone, connected to the detector 210a and to the transmitter 2 via the link 111 and configured for analyzing the signals received from the detector and for modifying the status of the PORT bit sent to the transmitter 2.

The strain gauge 210a is, for example, a film bonded to the headband and constituted by an electrical insulator (on the face of the film fixed the headband) upon which is arranged a metal wire provided with turns which extend along the headband. Alternatively, the strain gauge is a piezoelectric polymer film bonded onto the headband.

When the pilot places the boomset 200 on his head, the curvature of the headband 214 is modified with respect to its natural curvature and the strain gauge 210a deforms with respect to a neutral position obtained when the boomset is not being worn. The control means 210b transmit a signal with the PORT bit set to 1 to the transmitter 2 and the signals transmitted by the management unit 8 to the transmitter 2 via the channel C1 are transmitted to the ground station 5 for recording.

On the contrary, when the pilot removes the boomset, the headband 214 resumes its natural curvature and the strain gauge returns to its neutral position. The control means transmit a signal with the PORT bit set to 0 to the transmitter 2 so that the signals transmitted by the management unit 8 to the transmitter 2 via the channel C1 are not transmitted to the ground station 5.

Thus, according to the invention, only the audio data signals transmitted or received by an audio assembly 6a-6c being used by a pilot are transmitted to the ground station 5 for recording. Consequently, the audio data signals transmitted or received by the unused audio assemblies 6a-6c, and which are not however recorded by the CVR recorder 7, are not transmitted to the ground station 5. The use of the bandwidth of the satellite link 4 is therefore optimized.

In a variant, the strain gauge 210a is replaced by a heat sensor for detecting a contact with the skin of the pilot or an optical sensor (comprising a transmitter of the laser type arranged on an earphone and associated with a photodiode arranged on the other earphone) for detecting a masking when the boomset 200 is worn by the pilot.

Figure 4:
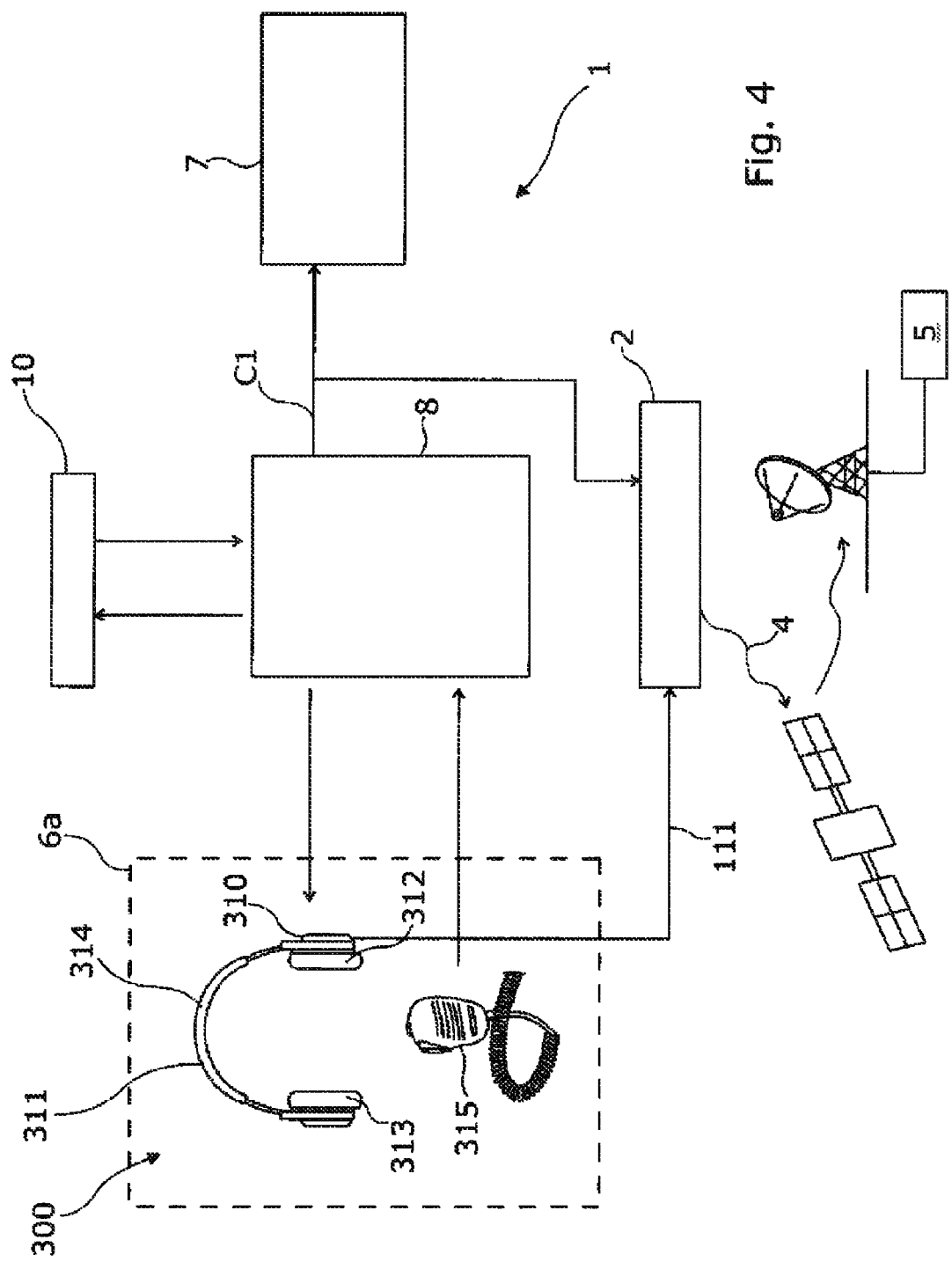
FIG. 4 is a view similar to FIG. 2, according to an embodiment of the invention in which an audio assembly comprises an audio headset and a microphone that are independent of each other.

With reference to FIG. 4, and in another embodiment of the invention, the audio assembly 6a comprises an audio headset 311 associated with a hand-held microphone 315 independent of the headset. The headset 311 is conventionally fitted with two loudspeakers, left 312 and right 313, connected by a headband 314 able to clamp the head of the pilot who is wearing the headset.

The detection system 310 is arranged on the headset, for example on the left earphone 312 and is identical to that one which was described above in relation to the headset of the boomset 200. In the same way as for the boomset 200, the detection system 310 of the audio device 300 sends a signal to the transmitter 2, the signal comprising a PORT bit set to 1 if the headset is worn or set to 0 if it is not worn.

Figure 5:
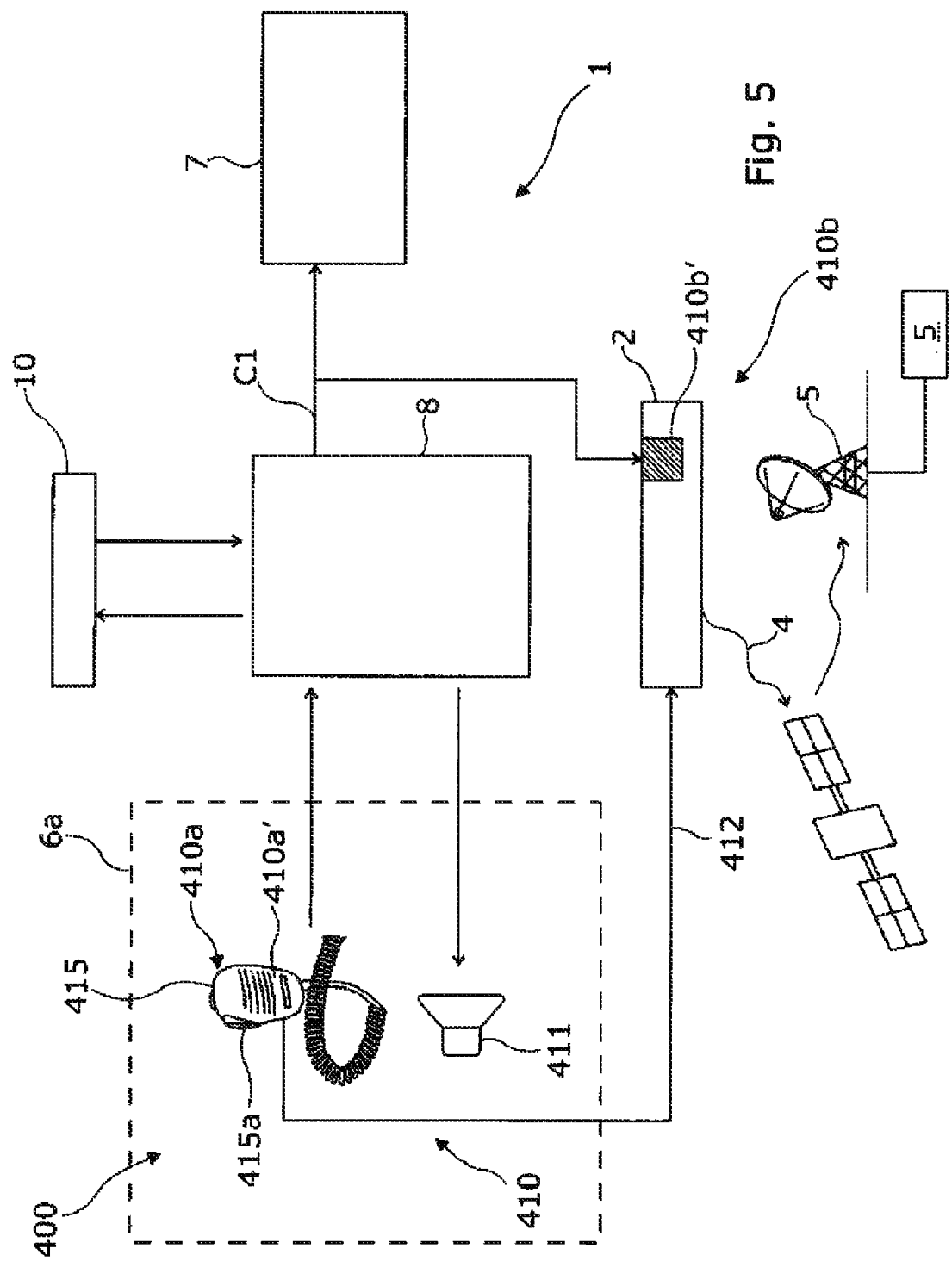
FIG. 5 is a view similar to FIG. 2, according to an embodiment of the invention in which an audio assembly comprises a microphone and a loudspeaker that are independent of each other.

In another embodiment of the invention, shown in FIG. 5, the audio assembly 6a comprises a hand-held microphone 415 and a loudspeaker 411 installed in the cockpit C of the aircraft. The microphone 415 comprises a PTT (Push To Talk) button 415a allowing the pilot to activate the microphone when that button is pressed.

The in-use detection system 410 connected to the transmitter comprises two parts, with a first part 410a associated with the microphone 415 for detecting the use of the audio assembly for the transmission of audio data signals and a second part 410b associated with the loudspeaker 411 for detecting the use of the audio assembly for receiving audio data signals.

The first part 410a comprises a contactor (not shown) associated with the PTT button 415a, and control means 410a' for example a microcontroller, both arranged in the microphone. The control means 410a' are connected to the connector and to the transmitter 2 via a link 412. The control means 410a' are configured for analyzing the signal received from the contactor and for sending a signal indicative of the in-use or not-in-use state of the microphone 415 to the transmitter 2. For example, the signal transmitted by the control means 410a' is a digital signal comprising a PORT bit set to 1 if the device is in use and to 0 if it is not in use.

When the pilot uses the microphone 415, he presses on the PTT button 415a which puts the contactor in a closed state: the transmitter 2 receives through the control means of the detector 410a' a signal with the PORT bit set at 1 and the audio data signals transmitted by the management unit 8 to the transmitter 2 via the channel C1 are transmitted to the ground station 5 for recording.

As a variant of the first part 410a, the control means 410a' are directly integrated in the management unit 8.

The second part 410b of the in-use detection system 410 comprises a comparator 410b' arranged in the transmitter 2. The comparator is configured for measuring the level of the audio signals received by the transmitter 2 via the channel C1 (the level of the signals measured by the comparator 410b' is proportional to the level of the signals received by the loudspeaker 411) and for comparing the measured level with a predetermined threshold:

the reception of a signal having a level greater than or equal to the threshold indicates a reception in progress of an audio data signal by the loudspeaker 411 and the communication between the communication system 1 and the ground station 5 is therefore activated; and the reception of a signal having a level less than the threshold indicates a reception in progress of background noise by the loudspeaker 411 and the communication between the communication system 1 and the ground station 5 is not activated.

In the description, it has been considered that the signal transmitted by the system for detecting the use of an audio assembly to the transmitter 2 is a digital signal comprising a PORT bit set to 1 if the device is in use and set to 0 if not. As a variant, the signal transmitted by the system for detecting the use of an audio assembly is an analogue signal of zero amplitude (a signal representing a not-in-use state of the audio assembly) if the audio assembly is not worn, and of non-zero amplitude greater than a threshold value (a signal representing the in-use state of the audio assembly) if the audio assembly is worn. The transmitter measures the amplitude of the signal transmitted by the system for detecting the use of an audio assembly and activates the transmission of data signals to the ground station 5 if the signal has an amplitude greater than the threshold value.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A communication system installed in an aircraft, said system comprising:
   a transmitter configured to transmit, via a satellite link, audio data signals to a ground recording station provided with memories for the recording of said data,
   at least one audio assembly per pilot of the aircraft configured to transmit and receive audio data signals,
   a CVR recorder, and
   an audio management unit connected to each audio assembly, to the CVR recorder, and to the transmitter, said audio management unit configured to transfer the audio signals from an audio assembly to both the transmitter and the CVR recorder,
   wherein each audio assembly comprises an in-use detection system connected to the transmitter and configured to transmit, to the transmitter, a signal representative of a state of said audio assembly as either an in-use signal or a not-in-use signal, wherein the in-use signal represents the state of said audio assembly while transmitting or receiving audio signals and wherein the not-in-use signal represents the state of said audio assembly while not transmitting or receiving audio signals,
   the transmitter configured to transmit the audio data signals received from the management unit to the ground recording station on reception of said in-use signal, wherein the in-use signal represents said audio assembly being used.

2. The communication system according to claim 1, wherein the audio assembly comprises an audio headset provided with two earphones connected by a headband, the in-use detection system comprises a detector and a control arranged on a headphone and connected to the detector and to the transmitter.

3. The communication system according to claim 2, wherein the detector comprises one of the following detectors:
   a strain gauge arranged on the headband;
   a heat sensor arranged on the headband; and
   an optical sensor.

4. The communication system according to claim 2, wherein the control comprises a microcontroller.

5. A method for the transmission, by means of a satellite link, of audio data signals from and aircraft to a ground recording station provided with memories for recording said data, said method being used by a communication system installed in an aircraft, said system comprising
   a transmitter configured to transmit audio data signals to a ground recording station provided with memories for recording said data,
   at least one audio assembly per pilot of the aircraft configured to transmit and
   receive audio data signals,
      a CVR recorder, and
      an audio management unit connected to each audio assembly, to the CVR recorder, and to the transmitter, said audio management unit configured to transmit the audio signals from an audio assembly to both the transmitter and the CVR recorder, each audio assembly comprising an in-use detection system connected to the transmitter and configured to transmit, to the transmitter, a signal representative of a state of the audio assembly as either an in-use signal or a not-in-use signal, wherein the in-use signal represents the state of said audio assembly while transmitting or receiving audio signals and wherein the not-in-use signal represents the state of said audio assembly while not transmitting or receiving audio signals, and
   wherein the method comprises the following steps:
      receiving by the transmitter the signal representative of the state of an audio assembly, said signal being transmitted by the in-use detention system of said audio assembly; and
      when said signal representative of the state of said audio assembly comprises an in-use signal, transmitting, by the transmitter to the ground recording station, the audio signals received and transmitted by said audio assembly; and,
      when said signal representative of the state of said audio assembly comprises an in-use signal and a not-in-use signal, transmitting the audio signals received and transmitted by said audio assembly to the CVR recorder.

* * * * *